United States Patent
Fu et al.

(12) 
(10) Patent No.: US 6,218,491 B1
(45) Date of Patent: Apr. 17, 2001

(54) COLORIMETRIC OR FLUOROMETRIC-DETECTABLE POLYMERS CONTAINING PENDANT AMINE GROUPS

(75) Inventors: Zhenwen Fu; Lorraine Holowach Keller, both of Lansdale; Barry Weinstein, Dresher, all of PA (US)

(73) Assignee: Rohm and Haas Company, Philadelphia, PA (US)

(*) Notice: Subject to any disclaimer, the term of this patent is extended or adjusted under 35 U.S.C. 154(b) by 0 days.

(21) Appl. No.: 09/246,659

(22) Filed: Feb. 5, 1999

Related U.S. Application Data

(63) Continuation of application No. 08/785,640, filed on Jan. 17, 1997, now Pat. No. 5,925,716.
(60) Provisional application No. 60/010,164, filed on Jan. 18, 1996.

(51) Int. Cl.[7] .............................. C08F 20/06; C08F 20/08; C08F 28/02
(52) U.S. Cl. ..................... 526/271; 526/287; 526/317.1; 526/318.3
(58) Field of Search ............................ 526/317.1, 318.2, 526/287, 240, 277, 278, 271, 204; 525/326.6, 328.5, 329.7, 351, 348, 318.3

(56) References Cited

U.S. PATENT DOCUMENTS

| 3,616,229 | 10/1971 | Wildi et al. . |
| 3,960,824 | 6/1976 | Hicks . |
| 4,195,128 | 3/1980 | Hilderbrand et al. . |
| 4,698,404 | 10/1987 | Cramm et al. . |
| 5,171,450 | 12/1992 | Hoots . |
| 5,413,719 | 5/1995 | Sivakumar et al. . |

FOREIGN PATENT DOCUMENTS

| 0475602A2 | 3/1992 | (EP) . |
| 03323840 | 11/1991 | (JP) . |

*Primary Examiner*—Christopher Henderson
(74) *Attorney, Agent, or Firm*—Thomas J. Howell

(57) ABSTRACT

Polymers having amine-thiol terminal moieties are provided. The amine-thiol terminal moieties are imparted by using amine-thiols as chain transfer agents in aqueous addition polymerizations.

The polymers are useful as mineral dispersants, as water-treatment additives for boiler waters, cooling towers, reverse osmosis applications, sugar refining, paper production, geo-thermal processes and oil wells, and as detergent additives acting as builders, anti-filming agents, dispersants, sequestering agents and encrustation inhibitors.

4 Claims, No Drawings

COLORIMETRIC OR FLUOROMETRIC-DETECTABLE POLYMERS CONTAINING PENDANT AMINE GROUPS

BACKGROUND

This is a continuing application of prior application Ser. No. 08/785,640 filed Jan. 17, 1997, now U.S. Pat. No. 5,925,716, issued Jul. 20, 1999. This application also claims benefit of provisional application 60/010,164 filed Jan. 18, 1996.

The present invention is directed to detectable polymers and methods for detecting polymers in aqueous systems. In particular, the present invention concerns water-soluble polymers containing a pendant amine group capable of reacting with amine-reactive labels.

Water-soluble polymers are used in many aqueous systems, for example, as mineral dispersants, as water-treatment additives for boiler waters, cooling towers, reverse osmosis applications, sugar refining, paper production, geothermal processes and oil wells, and as detergent additives acting as builders, anti-filming agents, dispersants, sequestering agents and encrustation inhibitors. In many of these aqueous systems it is desirable to know the level of polymer in the system. However, the level of active polymer is not simply a function of how much polymer has been added. The polymer may have adhered to a surface or may have flocculated out with sediment, or the polymer itself may have decomposed. Because polymers generally add cost to processes employing them, it is desirable to be able to use them efficiently.

One of the problems associated with detecting polymers in aqueous systems is that the polymers are generally present at very low levels, from 500 down to less than 5 parts per million (ppm). Another problem associated with detecting polymers in aqueous solutions is that the detection methods frequently lack selectivity and may give false results for components of the aqueous system other than polymers.

One attempt at overcoming these problems has been to use, in conjunction with the polymer, a tracer compound. The assumption behind this approach is that the tracer compound will be present in the aqueous system at a level proportional to the level of the polymer. However, this assumption is undermined by the fact that the fate of the tracer compound and the fate of the polymer in the aqueous system may differ.

Another approach to overcoming these problems is to incorporate into the polymer a detectable moiety. This has been accomplished, for example, by using a fluorescent monomer in preparing the polymer. This approach has the drawback of additional processing steps in preparing the fluorescent monomer. Also, the presence of the fluorescent moiety, which is usually a fairly bulky, hydrophilic group, may interfere with the performance characteristics of the resulting polymer. For example, many water treatment polymers have molecular weights below 10,000; the attachment of a fluorescent moiety can be a significant percentage of that, which can affect the function of the polymer.

U.S. Pat. No. 5,171,450 attempted to overcome these problems by recognizing that amine-containing dyes and amine-containing fluorescent compounds can be used with conventional water-treatment polymers which contain functional groups of carboxylic acids or amides. The amine-containing dyes or fluorescent compounds can be attached to these polymers via a transamidation reaction to create labeled or "tagged" polymers. These tagged polymers can be used and detected in aqueous systems. The drawbacks to this approach are that (1) the attachment of the fluorescent label may not be quantitative and (2) the presence of the label may interfere with the functioning of the polymer in the aqueous system.

The present invention overcomes the above problems by providing on the polymer not a detectable label but instead a site for the attachment of one, the label being attached during a reaction involving just a sample of the polymer removed for analysis. In this way the label is never attached to any polymer actually residing in the aqueous system in which it is being used.

STATEMENT OF INVENTION

Thus the present invention provides in a first aspect a polymer capable of detection by colorimetric or fluorimetric techniques, comprising at least one moiety containing a pendant amine group to which is attached an amine-reactive detectable label.

In a further aspect the invention provides a method for detecting a polymer in an aqueous system, comprising i) prior to addition to the aqueous system, reacting the polymer so that it comprises at least one moiety containing a pendant amine group;

ii) removing a sample of the aqueous system containing the polymer and adding a detectable label reactive with amines;

iii) maintaining the sample under such conditions that the detectable label reacts with the pendant amine group to become attached to the polymer; and iv) detecting the label.

Another aspect of the invention comprises the use of an amine-reactive detectable label which is attached to a pendant amine group on a polymer sample after removal of said sample from the polymer, to provide colorimetric or fluorimetric detectability to the polymer.

Thus it is pendant amine functionality that provides the site to which can be attached the label during analysis. The pendant amine moiety is not required on every monomer unit in the polymer: the molar ratio of moiety containing a pendant amine group to other monomer in the polymer (excluding the detectable label) may range from 1:3 to 1:300, more usually from 1:5 to 1:100.

DETAILED DESCRIPTION

A suitable method for imparting a pendant amine functionality to a polymer is to use a monomer containing a pendant amine functionality. Suitable monomers containing a pendant amine functionality include 2-aminoethylacrylate, 2-aminoethylmethacrylate, 2-aminoethylacrylamide, 2-aminoethylmethacrylamide, and homologues such as aminopropyl(meth)acrylamide. Latent amines such as vinylformamide may also be used. When a monomer containing a pendant amine functionality is used, the resulting polymer may contain one or more pendant amine groups.

Preferably, the pendant amine functionality which is imparted to the polymer is a terminal pendant amine functionality. Terminal pendant amine functionality can be imparted to a polymer by using one or more compounds which, when they function as a chain transfer agent, have a pendant amine group. Preferred compounds for imparting terminal amine functionality are amine-thiols.

Amine-thiols are compounds which contain, or those which under the conditions of the polymerization will contain: one or more amine groups ($-NR_1R_2$) wherein $R_1$ and $R_2$ are each independently selected from hydrogen and alkyl groups having from one to four carbon atoms; and one or more thiol groups (—SH). Preferably, the amine group is a primary amine (—NH$_2$). The amine-thiols suitable for the present invention are capable of functioning as a chain transfer agent for aqueous addition polymerizations; thereby imparting an amine-sulfide terminal moiety to the polymer chain. The amine-sulfide moiety is the residue of the amine-thiol resulting from the attachment of the sulfur group of the amine-thiol to the polymer chain.

Amine-thiols suitable for imparting terminal amine functionality include: amino acids containing one or more amines and one or more thiols; derivatives, peptides and polypeptides of amino acids containing one or more amines and one or more thiols; derivatives, peptides and polypeptides of amino acids containing one or more thiols and one or more protected amines wherein the protecting group is capable of being removed; and aminoalkyl thiols. A suitable amino acid is, for example, cysteine ("Cys"). Suitable derivatives of amino acids containing one or more amines and one or more thiols are, for example, N-alkyl and N,N-dialkyl substituted amino acids wherein the alkyl groups each contain from one to four carbon atoms. A suitable polypeptide of an amino acid containing one or more amines and one or more thiols is, for example, glutathione ("Glu"). A suitable derivative of an amino acid containing one or more thiols and one or more protected amines wherein the protecting group is capable of being removed is, for example, N-acyl cysteine ("N-Ac"). In addition, cystine may be used in the present invention under polymerization conditions which cause the cystine to cleave at the sulfur-sulfur bond to form at least one cysteine molecule. Suitable aminoalkyl thiols are, for example, as small as aminoethane thiol ("AET"), but it is preferred that the aminoalkyl thiols have at least three carbons. Other suitable aminoalkyl thiols are, for example, N-alkyl and N,N-dialkyl substituted aminoalkyl thiols wherein the alkyl groups each contain from one to four carbon atoms, such as, for example, N-butylaminoethanethiol, N,N-diethylaminoethanethiol and salts thereof. The one or more amine-thiols are generally used in an amount corresponding to a molar ratio of the one or more monomers to the one or more amine-thiols of from about 3:1 to about 300:1, preferably from about 5:1 to about 100:1.

The amine-thiols are used as chain transfer agents for polymerizations of one or more monomers. Preferably, the one or more monomers include monoethylenically unsaturated acids. Suitable monoethylenically unsaturated acids include, for example, mono-acids, di-acids or polyacids and the acids may be carboxylic acids, sulphonic acids, phosphonic acids, salts or combinations thereof If used, the monoethylenically unsaturated acids are preferably selected from one or more of acrylic acid, methacrylic acid, crotonic acid, vinylacetic acid, maleic acid, maleic anhydride, 1,2,3,6-tetrahydrophthalic anhydride, 3,6-epoxy-1,2,3,6-tetrahydrophthalic anhydride, 5-norbornene-2,3-dicarboxylic anhydride, bicyclo-[2.2.2]-5-octene-2,3-dicarboxylic anhydride, 3-methyl-1,2,6-tetrahydrophthalic anhydride, 2-methyl-1,3,6-tetrahydrophthalic anhydride, itaconic acid, mesaconic acid, fumaric acid, citraconic acid, 2-acrylamido-2-methylpropanesulfonic acid, allylsulfonic acid, allylphosphonic acid, allyloxybenzenesulfonic acid, 2-hydroxy-3-(2-propenyloxy)propanesulfonic acid, isopropenylphosphonic acid, isopro-penylsulfonic acid, vinylphosphonic acid, styrenesulfonic acid, vinylsulfonic acid and the alkali metal or ammonium salts thereof. Most preferably, the one or more monoethylenically unsaturated acids are acrylic acid, methacrylic acid, maleic acid and the alkali metal salts thereof. The one or more monoethylenically unsaturated acids preferably represent at least about 20 percent by weight of the total monomer weight, most preferably at least about 40 percent by weight of the total monomer weight.

In addition, the polymers may contain, as polymerized units, one or more monoethylenically unsaturated acid-free monomers. Suitable monoethylenically unsaturated acid-free monomers include (C$_1$–C$_4$)alkyl esters of acrylic or methacrylic acids such as methyl acrylate, ethyl acrylate, butyl acrylate, methyl methacrylate, ethyl methacrylate, butyl methacrylate and isobutyl methacrylate; hydroxyalkyl esters of acrylic or methacrylic acids such as hydroxyethyl acrylate, hydroxypropyl acrylate, hydroxyethyl methacrylate, and hydroxypropyl methacrylate. Other monoethylenically unsaturated acid-free monomers are acrylamides and alkyl-substituted acrylamides including acrylamide, methacrylamide, N-t-butylacrylamide, N-methylacrylamide, and N,N-dimethylacrylamide. Other examples of monoethylenically unsaturated acid-free monomers include acrylonitrile, methacrylonitrile, allyl alcohol, phosphoethyl methacrylate, 2-vinylpyridene, 4-vinylpyridene, N-vinyl-pyrrolidone, N-vinyl-formamide, N-vinylimidazole, vinyl acetate, and styrene. If used, the monoethylenically unsaturated acid-free monomers are preferably selected from one or more of ethyl acrylate, butyl acrylate, methyl methacrylate, butyl methacrylate, isobutyl methacrylate, hydroxyethyl acrylate, hydroxypropyl acrylate, hydroxyethyl methacrylate, acrylamide, methacrylamide, N-t-butylacrylamide, phosphoethyl methacrylate, vinyl acetate, and styrene. If used, the one or more monoethylenically unsaturated acid-free monomers preferably represent less than about 80 percent by weight of the total monomer weight, preferably less than about 60 percent by weight of the total monomer weight.

If desired, it is possible to incorporate polyethylenically unsaturated compounds into the polymerization. Polyethylenically unsaturated compounds function as crosslinking agents and will result in the formation of higher molecular weight polymers.

Preferably the polymers contain at least one amine-sulfide terminal moiety resulting from the attachment of the sulfur group of the amine-thiol to the polymer chain. Most preferably, the polymers contain an amine-sulfide terminal moiety or oxidised sulfide (e.g., sulfoxide, sulfone) as the only pendant amine moiety in the polymer. It is also preferred that the polymers are amine-sulfide terminated homopolymers, copolymers or terpolymers of acrylic acid or methacrylic acid and salts thereof More preferably, the polymers of the present invention are amine-sulfide terminated homopolymers of acrylic acid or methacrylic acid and salts thereof, or copolymers or terpolymers of acrylic acid or methacrylic acid or salts thereof with each other, maleic acid, maleic anhydride, 1,2,3,6-tetrahydrophthalic anhydride, 3,6-epoxy-1,2,3,6-tetrahydrophthalic anhydride, 5-norbornene-2,3-dicarboxylic anhydride, itaconic acid, fumaric acid, acrylamide, methacrylamide, N-t-butylacrylamide, N-methylacrylamide, N,N-dimethylacrylamide, 2-acrylamido-2-methylpropanesulfonic acid, methyl acrylate, ethyl acrylate, butyl acrylate, methyl methacrylate, butyl methacrylate, isobutyl methacrylate, hydroxyethyl acrylate, hydroxypropyl acrylate, hydroxyethyl methacrylate and salts thereof.

The polymers containing one or more pendant amine groups are prepared by a polymerization process which can be conducted as a cofeed, heel, semicontinuous or continuous process. Preferably, the polymerization is conducted as a cofeed process wherein substantially all of the one or more monomers, the initiator and the amine-thiol chain transfer agent are metered ("fed") into a polymerization reactor. Preferably, the one or more monoethylenically unsaturated monomers, the amine-thiol chain transfer agent and the initiators are introduced into the reaction mixture as separate streams which are fed linearly (i.e., at constant rates). If desired, the streams can be staggered so that one or more of the streams are completed before the others. Generally, the feeds are conducted for from 5 minutes to 5 hours, preferably from 30 minutes to 4 hours, and most preferably from 1 hour to 3 hours.

When the process of the present invention is run as a heel process, a portion of the one or more monoethylenically unsaturated monomers, the one or more amine-thiol chain transfer agents, and/or a portion of the initiators are initially added to the reactor. The remainder of any of these reactants are then fed into the reactor in the same manner as described above for the cofeed process.

The processes by which the polymers of the present invention are prepared are preferably aqueous processes, substantially free of organic solvents. The water may be introduced into the reaction mixture initially, as a separate feed, as the solvent for one or more of the other components of the reaction mixture or some combination thereof. Generally, the polymerizations have a final solids levels in the range of from about 20 percent to about 80 percent by weight of the reaction mixture, preferably in the range of from about 30 to about 70 percent by weight, and most preferably from about 40 to about 70 percent by weight of the reaction mixture.

The polymerization reaction is conducted at an elevated temperature which will depend on the choice of initiator, and target molecular weight. Generally, the temperature of the polymerization is up to the boiling point of the mixture although the polymerization can be conducted under pressure if higher temperatures are used. The reaction can be conducted under any suitable atmosphere such as for example, air, nitrogen or inert gas. Preferably, the temperature of the polymerization is from about 25 to about 110° C. and most preferably from about 40 to about 105° C.

Suitable initiators for preparing the polymers are any conventional water-soluble initiators. One class of suitable initiators are free-radical initiators such as hydrogen peroxide, certain alkyl hydroperoxides, dialkyl peroxides, persulfates, peresters, percarbonates, ketone peroxides and azo initiators. Specific examples of suitable free-radical initiators include hydrogen peroxide, t-butyl hydroperoxide, di-t-butyl peroxide, ammonium persulfate, potassium persulfate, sodium persulfate, t-amyl hydroperoxide, methylethyl ketone peroxide, 2,2'-azobis(2-amidinopropane), 2,2'-azobis(N,N'-dimethyleneisobutyramidine) dihydrochloride, 2,2'-azobis(2-amidinopropane) dihydrochloride, and 4,4'-azo-bis(4-cyanopentanoic acid). The free-radical initiators are typically used in amounts of from about 1 percent to about 50 percent based on the total monomer weight.

Water-soluble redox initiators may also be used. These initiators include, but are not limited to, sodium bisulfite, sodium sulfite, hypophosphites, hydroxyl amine sulfate, isoascorbic acid, sodium formaldehyde-sulfoxylate and the like, used with suitable oxidizing agents, such as the thermal initiators noted above. The redox initiators are typically used in amounts of from about 0.05 percent to about 10 percent, based on the weight of total monomer.

The pH of the polymerizing monomer mixture is preferably highly acidic, especially when using cysteine or aminoethane thiol as the chain transfer agent. For example, when cysteine is used as the chain transfer agent, the preferred pH is below about 4.0 and most preferably below about 2.0. Other amine-thiol chain transfer agents are less sensitive to pH and are preferably used at a pH below about 6. The pH of the polymerizing monomer mixture can be controlled by a buffer system or by the addition of a suitable acid or base. The preferred pH of the polymerizing monomer mixture may also be selected to suit the choice of any redox couple used as an initiator.

The polymerizing monomer mixture is preferably substantially free of any metal ions. The addition of metal ions to the polymerizing monomer mixture adds to the cost of the process, may necessitate a separation or purification step, may discolour the product, and introduces contaminants.

The process of preparing the polymers generally results in good conversion of the monomers into polymer product. However, if residual monomer levels in the polymer mixture are undesirably high for a particular application, their levels can be reduced by any of several techniques.

One common method for reducing the level of residual monomer in a polymer mixture is post-polymerization addition of one or more initiators or reducing agents which can assist scavenging of unreacted monomer.

Preferably, any post-polymerization additions of initiators or reducing agents are conducted at or below the polymerization temperature. The initiators and reducing agents suitable for reducing the residual monomer content of polymer mixtures are well known to those skilled in the art. Generally, any of the initiators suitable for the polymerization are also suitable for reducing the residual monomer content of the polymer mixture.

The level of initiators or reducing agents added as a means for reducing the residual monomer content of the polymer mixture should be as low as possible to minimize contamination of the product. Generally, the level of initiator or reducing agent added to reduce the residual monomer content of the polymer mixture is in the range of from about 0.1 to about 2.0, and preferably from about 0.5 to about 1.0 mole percent based on the total amount of polymerizable monomer.

The polymers are water-soluble. The water-solubility is affected by the molecular weight of the polymers and the relative amounts, and the hydrophilicity, of the monomer components incorporated into the polymer. Generally, the weight average molecular weights ($M_w$) of the polymers are up to about 50,000 preferably from about 500 to about 25,000 and most preferably from about 1,000 to about 15,000.

Amine-reactive detectable labels are compounds which are capable of attaching to the one or more pendant amines which are present on the polymer, and which, when thus attached, are detectable by fluorimetric or colorimetric techniques. Preferred amine-reactive detectable labels suitable for the present invention include 1-(dimethylamino)-5-naphthalenesulfonic acid ("dansyl"), dansyl halides such as dansyl chloride, 4-dimethylaminoazobenzene-4-sulfonic acid ("dabsyl"), dabsyl chloride, 3-benzoylquinoline-2-carboxaldehyde, 3-(4-carboxybenzoyl)quinoline-2-carboxaldehyde, 3-(2-furfoyl)quinoline-2-carboxaldehyde, 2,4,6-trinitrobenzene sulfonic acid, 2,4-dinitrofluorobenzene (Sanger's reagent) and ninhydrin.

The most preferred amine-reactive labels are dansyl chloride, which has the following structure:

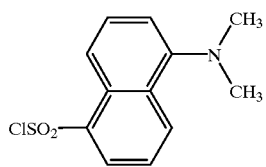

and dabsyl chloride, which has the following structure:

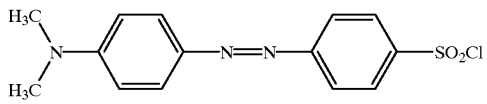

EXAMPLE 1

To a 300-milliliter, 4-neck flask equipped with a mechanical stirrer, reflux condenser, thermometer, and inlets for the gradual addition of monomer and initiator solution was added 75.0 grams of deionized water. The contents of the flask were stirred and heated to 92° C. Then, 0.20 grams of 2,2'-azobis(2-amidinopropane) dihydrochloride was added to the flask. An initiator solution of 0.80 grams of 2,2'-azobis (2-amidinopropane) dihydrochloride and 20.0 grams of deionized water was prepared. A chain transfer agent solution of 5.60 grams of cysteine, 5.4 g $H_2SO_4$ and 40.0 grams of deionized water was prepared. The chain transfer agent solution, initiator solution and 100.00 g of glacial acrylic acid were then fed into the flask linearly and separately while stirring over two hours. Once the additions were complete, the system was kept at 90–92° C. for 30 minutes. The system was then cooled to room temperature. The data appear in Table I below. The pH of the final mixture was 1.1

EXAMPLE 2

The procedure of Example 1 was repeated. The data appear in Table I below.

EXAMPLE 3

The procedure of Example 1 was repeated except that nitrogen was bubbled through the reaction mixture throughout the course of the polymerization. The data appear in Table I below.

EXAMPLE 4

The procedure of Example 1 was repeated except that the levels of 2,2'-azobis(2-amidinopropane) dihydrochloride were doubled. The data appear in Table I below.

EXAMPLE 5

To a 300-milliliter, 4-neck flask equipped with a mechanical stirrer, reflux condenser, thermometer, and inlets for the gradual addition of monomer and initiator solution was added 75.00 grams of deionized water, 0.17 grams of 50 percent by weight aqueous sodium hydroxide and 0.15 grams of 4,4'-azobis(4-cyanopentanoic acid). The contents of the flask were stirred and heated to 92° C. An initiator solution of 0.50 grams of 4,4'-azobis(4-cyanopentanoic acid), 0.36 grams of 50 percent by weight aqueous sodium hydroxide and 20.0 grams of deionized water was prepared. A chain transfer agent solution of 28.4 grams of glutathione, 6.70 grams of 50 percent by weight aqueous sodium hydroxide and 100.0 grams of deionized water was prepared. The chain transfer agent solution, initiator solution and 100.00 g of glacial acrylic acid were then fed into the flask linearly and separately while stirring over two hours. Once the additions were complete, the system was kept at 90–92° C. for 40 minutes. The system was then cooled to room temperature. The data appear in Table I below. The pH of the final mixture was 3.0.

EXAMPLE 6

The same procedure as Example 5 was followed except: to the flask was initially added 65.00 grams of deionized water, 0.22 grams of 50 percent by weight aqueous sodium hydroxide and 0.15 grams of 4,4'-azobis(4-cyanopentanoic acid); the initiator solution was 0.45 grams of 4,4'-azobis (4-cyanopentanoic acid), 0.40 grams of 50 percent by weight aqueous sodium hydroxide and 20.0 grams of deionized water; the chain transfer agent solution was 38.4 grams of glutathione, 9.0 grams of 50 percent by weight aqueous sodium hydroxide and 100.0 grams of deionized water was prepared; the monomer was 90.0 grams of acrylic acid.

EXAMPLE 7

A similar procedure as Example 5 was followed except that glutathione was used in an amount to provide a molar ratio of monomer to glutathione of about 30:1.

EXAMPLE 8

To a 1-liter, 4-neck flask equipped with a mechanical stirrer, reflux condenser, thermometer, and inlets for the gradual addition of monomer and initiator solution was added 120 grams of deionized water which was stirred and heated to 92° C. To the flask was added a solution of 0.2 grams of 50 percent by weight aqueous sodium hydroxide, 0.15 grams of 4,4'-azobis(4-cyanopentanoic acid) and 5.0 grams of deionized water. An initiator solution of 1.0 grams of 4,4'-azobis(4-cyanopentanoic acid), 0.62 grams of 50 percent by weight aqueous sodium hydroxide and 30.0 grams of deionized water was prepared. A chain transfer agent solution of 15.1 grams of N-acyl cysteine, 6.0 grams of 50 percent by weight aqueous sodium hydroxide and 50.0 grams of deionized water was prepared. The chain transfer agent solution, initiator solution and 200.00 g of glacial acrylic acid were then fed into the flask linearly and separately while stirring over two hours. Once the additions were complete, the system was kept at 90–92° C. for 30 minutes. The system was then cooled to room temperature. The data appear in Table I below.

EXAMPLE 9

The procedure of Example 8 was followed except: to the flask was initially added 125 grams of deionized water; when heated to 92° C. was added a solution of 0.3 grams of 50 percent by weight aqueous sodium hydroxide, 0.2 grams of 4,4'- azobis(4-cyanopentanoic acid) and 5.0 grams of deionized water; and the chain transfer agent solution was 30.2 grams of N-acyl cysteine, 12.0 grams of 50 percent by weight aqueous sodium hydroxide and 100.0 grams of deionized water. The data appear in Table I below.

EXAMPLE 10

The procedure of Example 1 was repeated except: the initiator solution was 0.80 grams of 2,2'-azobis(2-amidinopropane) dihydrochloride and 20.0 grams of deionized water; the chain transfer agent solution was 5.25 grams of aminoethane thiol and 30.0 grams of deionized water.

EXAMPLE 11

To a 300-milliliter, 4-neck flask equipped with a mechanical stirrer, reflux condenser, thermometer, and inlets for the gradual addition of monomer and initiator solution was added 65.00 grams of deionized water which was stirred and heated to 91° C. To the flask was added 0.1 grams of 4,4'-azobis(4-cyanopentanoic acid). An initiator solution of 0.90 grams of 4,4'-azobis(4-cyanopentanoic acid) and 30.0 grams of deionized water was prepared. A chain transfer agent solution of 16.8 grams of cysteine, 5.3 grams of sulfuric acid and 55.8 grams of deionized water was prepared. The chain transfer agent solution, initiator solution and 100.00 g of glacial acrylic acid were then fed into the flask linearly and separately while stirring over two hours. Once the additions were complete, the system was kept at 90–92° C. for 30 minutes. The system was then cooled to room temperature. The data appear in Table I below.

EXAMPLE 12

The procedure of Example 11 was followed except: the initiator solution was 0.36 grams of 4,4'-azobis(4-cyanopentanoic acid) and 20.0 grams of deionized water; the chain transfer solution was 5.6 grams of cysteine, 2.1 grams of sulfuric acid and 30.0 grams of deionized water.

EXAMPLE 13

The procedure of Example 11 was followed except: the initiator solution was 0.40 grams of 4,4'-azobis(4-cyanopentanoic acid) and 20.0 grams of deionized water; the chain transfer solution was 5.6 grams of cysteine, 5.4 grams of sulfuric acid and 40.0 grams of deionized water.

EXAMPLE 14

To a 1-liter, 4-neck flask equipped with a mechanical stirrer, reflux condenser, thermometer, and inlets for the gradual addition of monomer and initiator solution was added 220 grams of deionized water which was stirred and heated to 92° C. To the flask was added 0.25 grams of sodium persulfate dissolved in 5 grams of deionized water. An initiator solution of 2.50 grams of sodium persulfate and 30.0 grams of deionized water was prepared. A chain transfer agent solution of 14.0 grams of cysteine, 8.70 grams of 50 percent by weight aqueous sodium hydroxide and 90.0 grams of deionized water was prepared. The chain transfer agent solution, initiator solution and 100.00 g of glacial acrylic acid were then fed into the flask linearly and separately while stirring over 2.5 hours. Once the additions were complete, the system was kept at 90–92° C. for 20 minutes. A final solution of 0.3 grams of sodium persulfate and 20 grams of deionized water was added to flask. After 20 minutes, the system was then cooled to room temperature. The data appear in Table I below. The pH of the final mixture was 2.3. It is believed that the relatively high molecular weight of this product is a result of the amine-thiol reacting with the persulfate, thereby reducing the amount of persulfate capable of functioning as an initiator.

EXAMPLE 15

The procedure of Example 14 was followed except: to the flask was initially added 150 grams of deionized water; when heated to 92° C., 0.20 grams of 2,2'-azobis(2-amidinopropane) dihydrochloride was added: the initiator solution was 1.05 grams of 2,2'-azobis(2-amidinopropane) dihydrochloride and 60.0 grams of deionized water; the chain transfer agent solution was 22.5 grams of cysteine, 12.5 grams of 50 percent by weight aqueous sodium hydroxide and 60.0 grams of deionized water; 200.00 g of glacial acrylic acid were used; the solutions were fed into the flask linearly and separately while stirring over two hours; no attempt was made to reduce the residual monomer levels. The pH of the final mixture was 3.9.

The data appearing Table I are the weight average molecular weight ("$M_w$") and number average molecular weight ("$M_n$") as measured by aqueous gel permeation chromatography using a 4,500 $M_w$ poly(acrylic acid) standard. The chain transfer agent ("CTA") and the molar "Ratio" of the monomer to the amine-thiol are also listed.

TABLE I

| Example | CTA | $M_w$ | $M_n$ | Ratio |
| --- | --- | --- | --- | --- |
| 1 | Cys | 4500 | 3750 | 30:1 |
| 2 | Cys | 4720 | 3830 | 30:1 |
| 3 | Cys | 4480 | 3680 | 30:1 |
| 4 | Cys | 4870 | 3850 | 30:1 |
| 5 | Glu | 5130 | 4160 | 15:1 |
| 6 | Glu | 3810 | 3280 | 10:1 |
| 7 | Glu | 5960 | 4830 | 30:1 |
| 8 | N-Ac | 5960 | 4830 | 30:1 |
| 9 | N-Ac | 3900 | 3310 | 15:1 |
| 10 | AET | 4700 | 3860 | 30:1 |
| 11 | Cys | 2570 | 2300 | 10:1 |
| 12 | Cys | 7490 | 5180 | 30:1 |
| 13 | Cys | 4790 | 3940 | 30:1 |
| 14 | Cys | 91700 | 49960 | 30:1 |
| 15 | Cys | 13200 | 7900 | 15:1 |

ATTACHMENT OF DETECTABLE LABEL TO POLYMERS

Dansyl chloride was attached to amine-containing polymers in the following manner. Polymer solutions were prepared by dissolving, in an amber vial, approximately 5 milliliters of polymer in 100 milliliters of deionized water. The pH of the polymer solutions was adjusted to 9.0–9.5 with 1 molar (M) aqueous sodium carbonate. To the polymer solution was added a dansyl chloride solution (10 milligrams dansyl chloride dissolved in 10 milliliters of acetone) to a level of 200 microliters of dansyl chloride solution per 10 milliliters of polymer solution. The mixture was placed on a sample shaker or roller for 2–4 hours at room temperature.

Dabsyl chloride was attached to amine-containing polymers in the following manner. The pH of the polymer samples was adjusted to 9.0–9.5 with 1M aqueous sodium carbonate. An equal volume of dabsyl chloride solution (3.3 milligrams dabsyl chloride dissolved in 1 milliliter of acetone) was added to the polymer solution. The mixture was placed on a sample shaker or roller for 2–4 hours at room temperature.

After the detectable labels were attached to the pendant amine groups of the polymers, the polymer samples were dialyzed to remove any excess (unbound) label and label which might have attached to residual amine-thiol (if any). The samples were dialyzed via ultrafiltration using membranes with a cutoff of 1,000 $M_w$.

The labelled polymers were detected by fluorimetric methods using a SPEX Industries, Inc. Fluorolog 2 series spectrofluorometer using right-angle detection. Fluorescence was measured by photon counting and is reported as counts per second ("cps"). Samples were placed in a 1 centimeter by 1 centimeter by 4 centimeter quartz cuvette and were subjected to an excitation source (xenon lamp) of radiation having a wavelength of 335 nanometers. The fluorescence reported in Table II below is the emission fluorescence measured at 560 nanometers.

TABLE II

| Sample | Concentration (ppm) | Fluorescence |
|---|---|---|
| Example 7* | 8700 | 0.42# |
| Example 7 | 14000 | 2,390,500 |
| | 540 | 168,940 |
| | 20 | 6,833 |
| | 1 | 470 |
| Example 1 | 5000 | 336130 |
| | 500 | 45,912 |
| | 50 | 4,858 |
| | 30 | 2,915 |
| | 20 | 2,156 |
| | 10 | 1132 |
| | 1 | 180 |
| Example 10 | 30 | 7135 |

\* = sample was not dansylated.
Absorbance at 254 nanometers

USE OF THE POLYMERS AS WATER-TREATMENT ADDITIVES

Polymers containing pendant amine functionality were evaluated as water-treatment additives in the following manner.

A kaolin suspension was prepared by adding to a clean, dry mixing cup: (a) 430 milliliters of water having 200 ppm of $CaCl_2$ as $CaCO_3$, and (b) 0.43 grams of Hydrite UF kaolin. The suspension was mixed on a multimixer for 10 minutes. The suspension was transferred to a clean dry glass jar and the pH of the suspension was adjusted to 8.0 with 0.05N sodium hydroxide while stirring. The suspension was then divided into 100 milliliter samples. To a 100 milliliter sample was added either (a) 0.2 milliliters of a 25 percent by weight aqueous polymer solution to form a kaolin suspension containing 5.0 ppm polymer polymer or (b) 0.4 milliliters of a 25 percent by weight aqueous polymer solution to form a kaolin suspension containing 10.0 ppm polymer polymer.

In Table III below, the bottom two entries (#7 and #8) are comparative examples of polymers without pendant amine functionality. Higher values for dispersancy signify better performance.

TABLE III

| | | | | | Kaolin Dispersancy (NTU) | | |
|---|---|---|---|---|---|---|---|
| SAMPLE | DP | Mw | Mn | CTA | 5 ppm | 10 ppm | 20 ppm |
| 1 - PAA | 15 | 5130 | 4160 | glutathione | 97 | 120 | 262 |
| 2 - PAA | 10 | 3810 | 3280 | glutathione | 120 | 187 | 230 |
| 3 - PAA | 10 | 2570 | 2300 | cysteine | 83 | 170 | 388 |
| 4 - PAA | 30 | 4790 | 3940 | cysteine | 75 | 73 | 164 |
| 5 - PAA | | 2000 | | bisulfite | 125 | 309 | 530 |
| 6 - PAA | | 4500 | | bisulfite | 99 | 99 | 49 |
| 7 - PMal* | | 1000 | | | 45 | 55 | 50 |
| 8 - PBTC* | | 270 | | | 27 | 31 | 50 |

\*= comparative samples
note:
DP = mols of monomer/mols of CTA
PAA = poly(acrylic acid)
Sample 7 = Belclene 200, a poly(maleic acid)
Sample 8 = Bayhabit AM, 2-phosphonobutane-1,2,4-tricarboxylic acid, available from Mobay Chemical The results above show that the polymers containing pendant amine functionality performed as well as those without.

Calcium Carbonate ($CaCO_3$) Anti-precipitation Test

Three stock solutions were prepared as follows:

1: Alkalinity solution: 2.14 grams $NaHCO_3$ and 1.35 grams $Na_2CO_3$ were added to a volumetric flask and were diluted to a total volume of 2.00 liters with deionized water.

2. Hardness solution: 3.74 grams of $CaCl_2 \cdot 2H_2O$ and 1.53 grams of $MgSO_4$ were added to a volumetric flask and were diluted to a total volume of 2.00 liters. To this solution was added 5 drops of 2N HCl.

3. Polymer or Phosphonate solutions: A polymer sample (or 2-phosphonobutane-1,2,4-tricarboxylic acid) was diluted to 0.1 percent by weight solids with deionized water and the pH was adjusted to 5.0–6.0 with 1 percent by weight aqueous NaOH.

From the three stock solutions above were prepared:

1. A control solution of 50 milliliters (mls) of alkalinity solution and 50 mls of hardness solution.

2. A 100% inhibited solution of 50 mls of hardness solution and 50 mls of deionized water.

3. A test solution of 50 mls of alkalinity solution, 50 mls of hardness solution and 0.7 mls of polymer solution.

Into separate glass jars were added the control solution, the 100% inhibited solution and the test solution. The jars were placed in a constant temperature water bath set at 54° C. and allowed to stand for 20 hours. The jar was then removed from the water bath and the contents were immediately filtered through a 0.22 micron filter into another clean, dry jar. 40.0 grams of the filtered solution, 0.5 mls of 0.05N HCl and 0.1 grams of Calgon brand certified calcium indicating powder (catalog #R-5293) were added to an Ehrlenmeyer flask and titrated with Calgon brand certified hardness titrating solution 20 (catalog #R-501 1). The percent $CaCO_3$ inhibition was calculated as follows where each of the values is the number of milliters of titrating solution needed to reach the endpoint against the other solutions:

$$\% \text{CaCO}_3 \text{ inhibition} = 100 \times \frac{(\text{test solution}) - (\text{control solution})}{(100\% \text{ inhibited solution}) - (\text{control solution})}$$

The $CaCO_3$ inhibition property of the polymer was measured in this manner and the data appear in Table IV below as the average of two results.

The data in Table IV (higher numbers for inhibition equate to superior performance) show that the polymers of the present invention are useful water treatment additives and are effective for inhibiting calcium carbonate formation in an aqueous system.

TABLE IV

| SAMPLE | Composition | Mw | % $CaCO_3$ Inhibition Avg of 2 values |
|---|---|---|---|
| 5 | PAA - bisulfite | 2000 | 66.0 |
| 5 | PAA - bisulfite | 2000 | 76.9* |
| 6 | PAA - bisulfite | 4500 | 71.0 |
| 7 | PMal | 1000 | 75.2 |
| 7 | PMal | 1000 | 69.9 |
| 7 | PMal | 1000 | 72.7 |
| 8 | PBTC | 270 | 88.1* |
| 8 | PBTC | 270 | 89.7 |
| 9 | PAA - glutathione | 5130 | 73.8 |
| 10 | PAA - cysteine | 5960 | 76.3 |

\* = Average of 4 values
PAA = poly(acrylic acid)
Sample 7 = Belclene 200, a poly(maleic acid)
Sample 8 = Bayhabit AM, 2-phosphonobutane-1,2,4-tricarboxylic acid available from Mobay Chemical Barium sulphate ($BaSO_4$) Anti-precipitation Test The following solutions were made up:
1. Inhibitor solution: 1% polymer solution in 50 ml water, neutralized to pH 6.1 if necessary.
2. Acetate buffer solution: 13.5 g acetic acid plus 34 g sodium acetate·$3H_2O$ plus water to 250 ml.

|  | "North Sea" stock solution | "Formation" stock solution |
| --- | --- | --- |
| $CaCl_2.2H_2O$ | 3.14 g | 7.78 g |
| $MgCl_2.6H_2O$ | 22.87 | 1.92 |
| KCl | 1.75 | 6.98 |
| NaCl | 47.91 | 142.36 |
| $NaHCO_3$ | 0.342 | — |
| $Na_2SO_4$ | 7.69 | — |
| $SrCl_2.6H_2O$ (1%) | 4.80 | — |
| $SrCl_2.6H_2O$ (10%) | — | 6.7 |
| $BaCl_2.2H_2O$ (10%) | — | 37.56 |

The above solutions were each made up in 2 liters of polished deionised water.

Samples to be tested were made up in jars as follows.
1. 0.65 ml 1% inhibitor solution 1 ml sodium acetate buffer solution 80 ml "Formation" water
2. 20 ml "North Sea" water These samples were placed in a water bath at 95° C. for 45 minutes, at which point the contents of the North Sea water sample were poured into the jar containing the Formation water sample to provide an 80:20 Formation water: Sea water ratio sample. The sample was placed in the water bath for a further two hours. The sample was then removed from the water bath, and swirled gently to suspend the scale. It was then poured into a pressure filter containing a 22 μm filter. The jar was rinsed twice with 30 ml of DI water, and the rinsate filtered also. The collected scale was dried in an oven at 120° C. for one and a half hours, then placed in a dessicator to cool, after which it was weighed.

Results are shown in Table V below. The less scale collected, the better the performance of the polymer as an inhibitor. The results show that the polymers treated according to the present invention function as well as those not containing the label.

TABLE V

| Sample | Composition | Mw | mg scale |
| --- | --- | --- | --- |
| No Polymer | — | — | 124.1 |
| 1 | PAA-glutathio | 5130 | 25.0* |
| 4 | PAA-cysteine | 4790 | 11.0* |
| 6 | PAA-bisulf | 4500 | 14.0 |
| 10 | PAA-cysteine | 5960 | 12.0* |
| 11 | PAA-bisulf | 2700 | 26.7 |
| 12 | PAA-bisulf | 5300 | 7.0 |
| 13 | PAA-bisulf | 7400 | 11.6 |
| 14 | PAA-glutathio | 6970 | 15.0* |

TABLE V-continued

| Sample | Composition | Mw | mg scale |
| --- | --- | --- | --- |
| 15 | DETPMP | 573 | 5.4 |
| 16 | PAA-hypophosph | 3000 | 29.0 |

* Note: single data point
Sample 15 = Dequest 2060, diethylenetriamine penta(methylene phosphonic acid), available from Monsanto Corp
Sample 16 = Bellasol S40, a phosphinocarboxylic acid, available from FMC Corp

We claim:

1. Polymer capable of detection by colorimetric or fluorimetric techniques, comprising a detectable terminus containing a pendant amine group to which is attached an amine-reactive detectable label, wherein the molar ratio of polymer to amine-reactive detectable label is essentially 1:1; wherein the pendant amine group is an amine-sulfide moiety present in a molar ratio of 1:3 to 1:300 relative to other monomer in the polymer, prior to attachment of the amine-reactive detectable label: and wherein the polymer comprises as polymerized units, monoethylenically unsaturated acids selected from one or more of acrylic acid, methacrylic acid, crotonic acid, vinylacetic acid, maleic acid, maleic anhydride, 1,2,3,6-tetrahydrophthalic anhydride, 3,6-epoxy-1,2,3,6-tetrahydrophthalic anhydride, 5-norbornene-2,3-dicarboxylic anhydride, bicyclo[2.2.2]-5-octene-2,3-dicarboxylic anhydride, 3-methyl-1,2,6-tetrahydrophthalic anhydride, 2-methyl-1,3,6-tetrahydrophthalic anhydride, itaconic acid, mesaconic acid, fumaric acid, citraconic acid, 2-acrylamido-2-methylpropanesulfonic acid, allylsulfonic acid, allylphosphonic acid, allyloxybenzenesulfonic acid, 2-hydrox-3-(2-propenyloxy)-propanesulfonic acid, isopropenylsulfonic acid, isopropenylphosphonic acid, vinylphosphonic acid, styrenesulfonic acid, vinylsulfonic acid and alkali metal or ammonium salts thereof.

2. Polymer according to claim 1 wherein the pendant amine group contains an amino portion which is a primary amine.

3. Polymer according to claim 2 wherein the amine-sulfide moiety derives from an amine-thiol which comprises an amino acid containing one or more amines and one or more thiols; a derivative, peptide or polypeptide of an amino acid containing one or more amines and one or more thiols; a derivative, peptide or polypeptide of an amino acid containing one or more thiols and one or more protected amines wherein the protecting group is capable of being removed; or an aminoalkyl thiol.

4. Polymer according to claim 1 further comprising, as polymerized units, monoethylenically unsaturated acid-free monomers selected from one or more of ethyl acrylate, butyl acrylate, methyl methacrylate, butyl methacrylate, isobutyl methacrylate, hydroxyethyl acrylate, hydroxypropyl acrylate, hydroxyethyl methacrylate, acrylamide, methacrylamide, N-t-butylacrylamide, phosphoethyl methacrylate, vinyl acetate and styrene.

\* \* \* \* \*